US010228574B2

(12) United States Patent
Tillotson (10) Patent No.: US 10,228,574 B2
(45) Date of Patent: Mar. 12, 2019

(54) SYSTEM AND METHOD FOR PROTECTION OF EYES AGAINST LASER LIGHT

(71) Applicant: The Boeing Company, Chicago, IL (US)

(72) Inventor: Brian Tillotson, Kent, WA (US)

(73) Assignee: The Boeing Company, Chicago, IL (US)

( * ) Notice: Subject to any disclaimer, the term of this patent is extended or adjusted under 35 U.S.C. 154(b) by 210 days.

(21) Appl. No.: 15/048,864

(22) Filed: Feb. 19, 2016

(65) Prior Publication Data

US 2017/0242272 A1  Aug. 24, 2017

(51) Int. Cl.
  *G02C 7/10* (2006.01)
  *A61F 9/02* (2006.01)

(52) U.S. Cl.
  CPC .............. *G02C 7/105* (2013.01); *A61F 9/022* (2013.01)

(58) Field of Classification Search
  CPC ........ G02C 7/104; G02C 7/105; G02C 7/107; G02C 7/108; G02C 7/10; G02C 7/101; G02C 7/102; A61F 9/022; A61F 9/023; A61F 9/025; A61F 9/065; A61F 9/067
  USPC ............. 351/44, 47, 48, 885, 890, 891, 892, 351/159.59, 159.6; 2/12, 13, 426–454; 359/601, 614, 722, 892
  See application file for complete search history.

(56) References Cited

U.S. PATENT DOCUMENTS

| 4,836,647 A * | 6/1989 | Beard | H04N 13/0431 359/464 |
| 2012/0099188 A1* | 4/2012 | Akozbek | G02B 5/208 359/360 |

OTHER PUBLICATIONS

Wikipedia, "Mirrored Sunglasses," retrieved Feb. 18, 2016.
Wikipedia, "Laser Protection," retrieved Jan. 23, 2016.
Aero Magazine, First Quarter, 2010, pp. 11-15.

* cited by examiner

*Primary Examiner* — Ricky L Mack
*Assistant Examiner* — Gary O'Neill (57) ABSTRACT

An eye protection system may include a first lens, a second lens, and a lens support. The first lens may filter light of one or more first wavelengths. The second lens may filter light of one or more second wavelengths. At least one of the one or more first wavelengths may be different than at least one of the one or more second wavelengths. The lens support may position the first lens and the second lens in side-by-side arrangement respectively in front of a first eye and a second eye of a wearer in a manner respectively preventing the one or more first wavelengths and the one or more second wavelengths from being respectively received by the first eye and the second eye.

19 Claims, 7 Drawing Sheets

SYSTEM AND METHOD FOR PROTECTION OF EYES AGAINST LASER LIGHT

FIELD

The present disclosure relates to eye protection and, more particularly, to a system and method for protection of the eyes against laser light.

BACKGROUND

Lasers pose an increasing threat to the safety of ground transportation, air transportation, and other activities. For example, soldiers, pilots, and first responders increasingly face the threat of lasers shining in their eyes and causing temporary and occasionally permanent loss of vision. Loss of vision is especially dangerous for certain groups of people such as the flight crew of an aircraft. A hand-held laser device (e.g., a laser pointer) pointed upwardly toward an aircraft at relatively high altitudes may result in glare disruption of the flight crew. For an aircraft at lower altitudes, a laser beam may result in temporary flash blindness of the flight crew. Depending upon the intensity and wavelength of the laser beam, a laser beam at short range may pose the risk of eye damage to the flight crew including temporary or permanent blindness. In addition to the above-mentioned risks that lasers pose to the flight crew of an aircraft, certain other groups of people are at risk for vision impairment due to lasers such as policemen and firemen during an emergency response involving high-speed driving.

Current devices for vision protection against laser light include laser safety goggles for use in laser laboratories. Such laser safety goggles are typically designed to block only one wavelength of light or a narrow band of wavelengths. Unfortunately, laser attacks may span a fairly wide range of wavelengths. Current devices may also include safety goggles that block a wide range of wavelengths. Unfortunately, such safety goggles are typically heavy, costly, and may block such a large portion of the visible spectrum that it may be difficult or even dangerous for the wearer to operate a vehicle. For example, such safety goggles would prevent pilots from distinguishing a red light from a green light to know when aircraft systems are failing, or prevent pilots from differentiating between airport beacons, approach lights, runway lights, and taxiway lights.

As can be seen, there exists a need in the art for an eye protection system and method for protection against laser light and which is low cost, lightweight, and allows for the safe operation of a vehicle in the event of a laser attack.

SUMMARY

The above-noted needs associated with eye protection against lasers are specifically addressed and alleviated by the present disclosure which provides an eye protection system having a first lens, a second lens, and a lens support. The first lens may filter light of one or more first wavelengths. The second lens may filter light of one or more second wavelengths. At least one of the one or more first wavelengths may be different than at least one of the one or more second wavelengths. The lens support may position the first lens and the second lens in side-by-side arrangement respectively in front of a first eye and a second eye of a wearer in a manner respectively preventing the one or more first wavelengths and the one or more second wavelengths from being respectively received by the first eye and the second eye.

In a further embodiment, an eye protection system may have a first lens configured to filter light in a first wavelength band, and a second lens configured to filter light in a second wavelength band. At least a portion of the first wavelength band may be different than at least a portion of the second wavelength band. The lens support may position the first lens and the second lens in side-by-side arrangement respectively in front of the first eye and the second eye of a wearer in a manner respectively preventing the first wavelength band and the second wavelength band from being respectively received by the first eye and the second eye.

Also disclosed is an eye protection method which may include the step of positioning a first lens and a second lens in side-by-side arrangement in front of a first eye and a second eye of a wearer. The method may also include filtering light using the first lens and/or the second lens by respectively performing at least one of the following: (1) filtering, using the first lens, light of one or more first wavelengths in a manner preventing the one or more first wavelengths from being received by the first eye, and (2) filtering, using the second lens, light of one or more second wavelengths in a manner preventing the one or more second wavelengths from being received by the second eye. At least one of the one or more first wavelengths may be different than at least one of the one or more second wavelengths.

The features, functions and advantages that have been discussed can be achieved independently in various embodiments of the present disclosure or may be combined in yet other embodiments, further details of which can be seen with reference to the following description and drawings below.

BRIEF DESCRIPTION OF THE DRAWINGS

These and other features of the present disclosure will become more apparent upon reference to the drawings wherein like numbers refer to like parts throughout and wherein.

DETAILED DESCRIPTION

Figure 1:
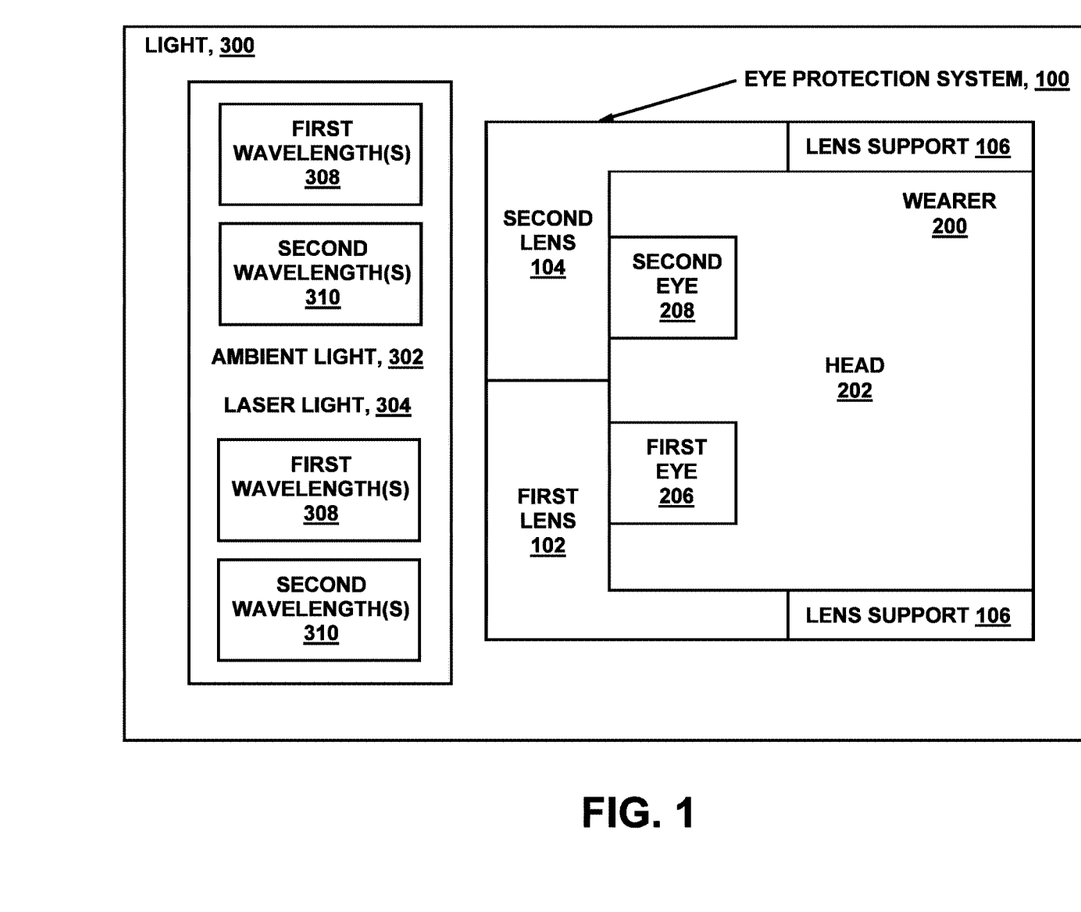
FIG. 1 is a block diagram of an eye protection system having a first lens and a second lens positioned side-by-side for respectively protecting a first eye (e.g., a left eye) and a second eye (e.g., a right eye) and wherein the first lens is configured to filter one or more first wavelengths of light and the second lens is configured to filter one or more second wavelengths of light.

Referring now to the drawings wherein the showings are for purposes of illustrating various embodiments of the present disclosure, shown in FIG. 1 is a block diagram of an eye protection system 100 having a first lens 102 and a second lens 104 supported or mounted in side-by-side arrangement by a lens support 106. The lens support 106 is configured to position the first lens 102 and the second lens 104 respectively immediately in front of a first eye 206 (e.g., a left eye) and a second eye 208 (e.g., a right eye) of a wearer 200 of the lens support 106. The first lens 102 may filter one or more first wavelengths 308 of light 300 and the second lens 104 may filter one or more second wavelengths 310 of light 300 which may be different than the first wavelengths 308. The first lens 102 and the second lens 104 may filter light 300 in a manner respectively preventing the first wavelength(s) 308 and the second wavelength(s) 310 from being respectively received by the first eye 206 and the second eye 208. In this regard, the first lens 102 and the second lens 104 may filter wavelengths that are in different portions of the spectrum. Together, the first lens 102 and the second lens 104 may cover substantially all wavelengths of light 300 anticipated to be encountered in a situation during which laser light 304 may pose a risk to the wearer's vision. Advantageously, the first lens 102 and the second lens 104 may be relatively thin and therefore lightweight and comfortable to wear over extended periods of time while still allowing for sufficient light of unfiltered wavelengths to reach the wearer's eyes to allow the wearer to visualize their environment and safely perform various duties such as driving a vehicle, piloting an aircraft, and other activities.

Figure 4:
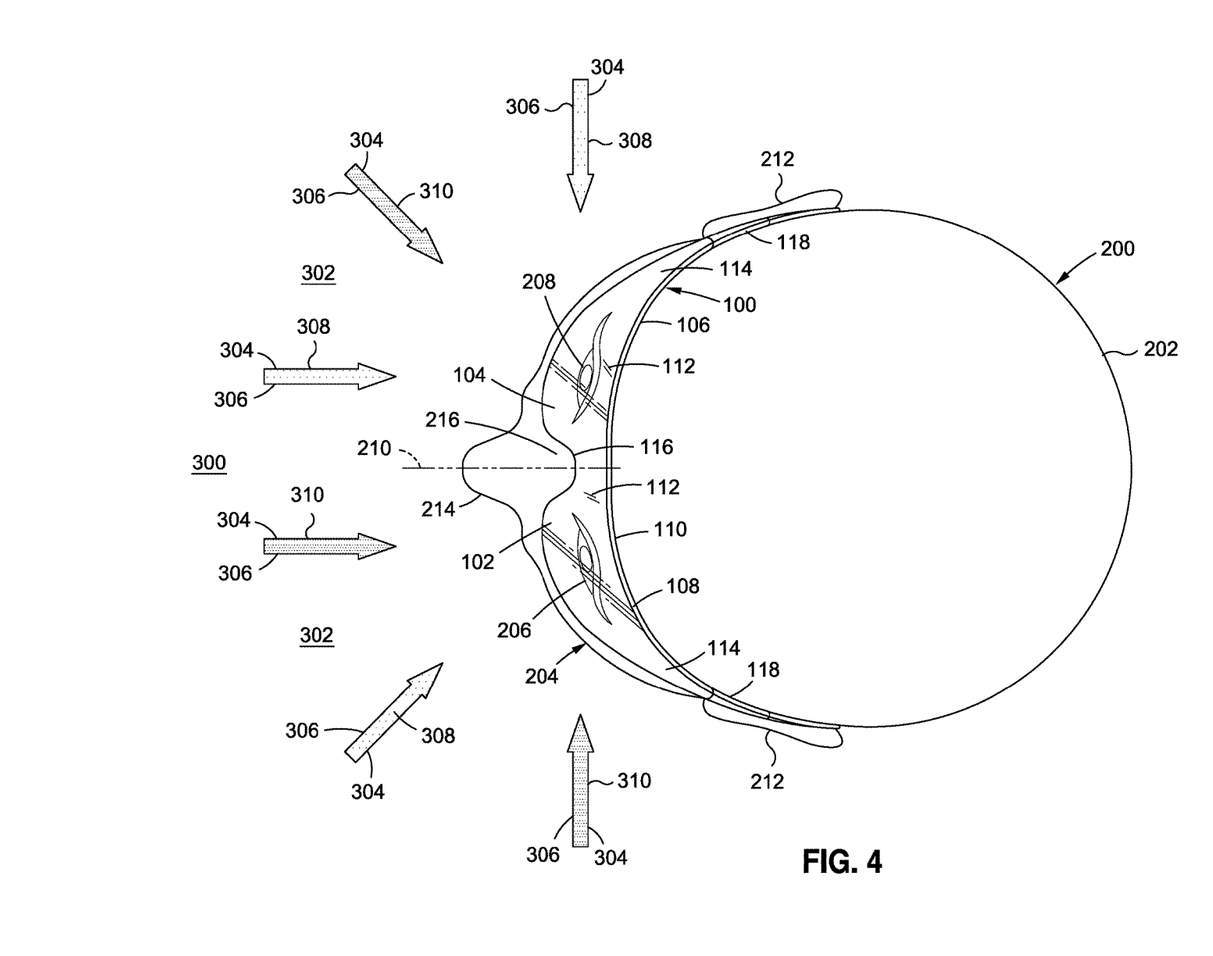
FIG. 4 is a top view of the eye protection system of FIGS. 2-3 and illustrating laser light directed toward the first eye and the second eye at different angles.

The first lens 102 and the second lens 104 may each may filter light 300 in the respective first wavelength(s) 308 (FIG. 1) and second wavelength(s) 310 by absorbing, reflecting, and/or blocking the passage of such first wavelength(s) 308 and second wavelength(s) 310 through the respective first lens 102 and second lens 104 (FIG. 1). The first lens 102 and the second lens 104 may be transparent to light 300 in wavelengths respectively other than the first wavelength(s) 308 and the second wavelength(s) 310. The first lens 102 and the second lens 104 may filter ambient light 302 which may include laser light 304 (e.g., coherent light) emitted by one or more laser beams 306 (FIG. 4). Such laser light 304 may be directed by one or more laser beams 306 toward the wearer 200 or such laser light 304 (FIG. 1) may be reflected off of objects and/or scattered and may ultimately impinge on the first lens 102 and/or the second lens 104 for filtering. In addition, the first lens 102 and the second lens 104 may filter white light (e.g., non-coherent light) such as from natural sources and/or from artificial sources. Natural sources may include sunlight, moonlight, starlight, and other natural sources. Artificial sources of light may include light produced by incandescent bulbs, fluorescent bulbs, light from light-emitting-diodes (LEDs), instrument lights of a vehicle (e.g., flight instrument lights in an aircraft cockpit), airport lights (e.g., runway lights), and other artificial light sources.

The first wavelength(s) 308 and the second wavelength(s) 310 (FIG. 1) may be in the ultraviolet spectrum, the visible spectrum, and/or the infrared or near-infrared spectrum. The ultraviolet spectrum may include radiation with wavelengths in the range of approximately 10-400 nm. The visible spectrum may include radiation with wavelengths in the range of approximately 400-750 nm. The near-infrared spectrum may include radiation with wavelengths in the range of approximately 750-1400 nm. The first lens 102 and/or the second lens 104 may be transparent to light 300 in at least a portion of the ultraviolet spectrum, the visible spectrum, and/or the infrared spectrum in wavelengths respectively other than the first wavelength(s) 308 (FIG. 1) and the second wavelength(s) 310.

Figure 2:
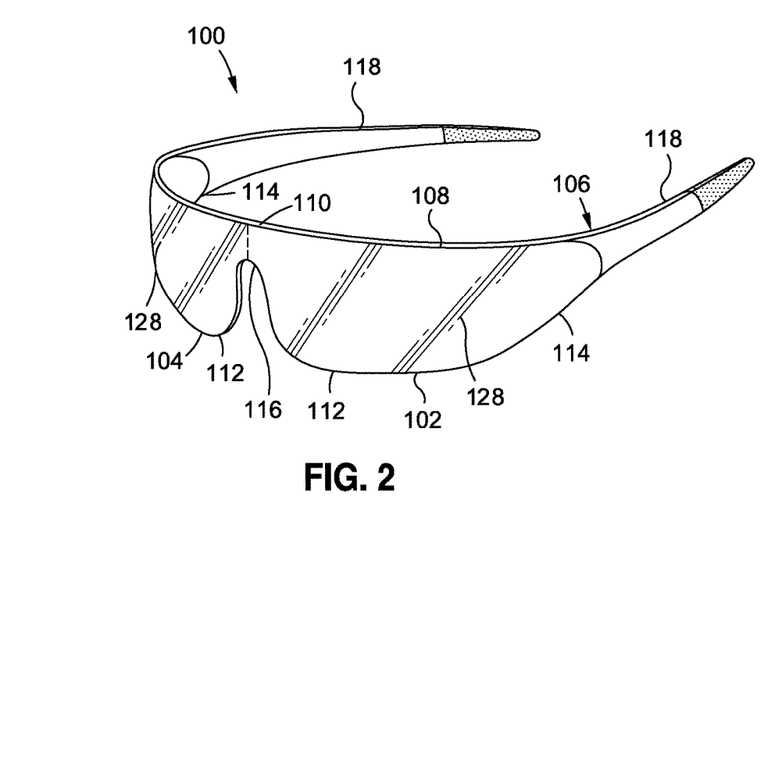
FIG. 2 is a perspective view of an example of an eye protection system having a lens support configured as lens frame for supporting the first lens and the second lens.
Figure 3:
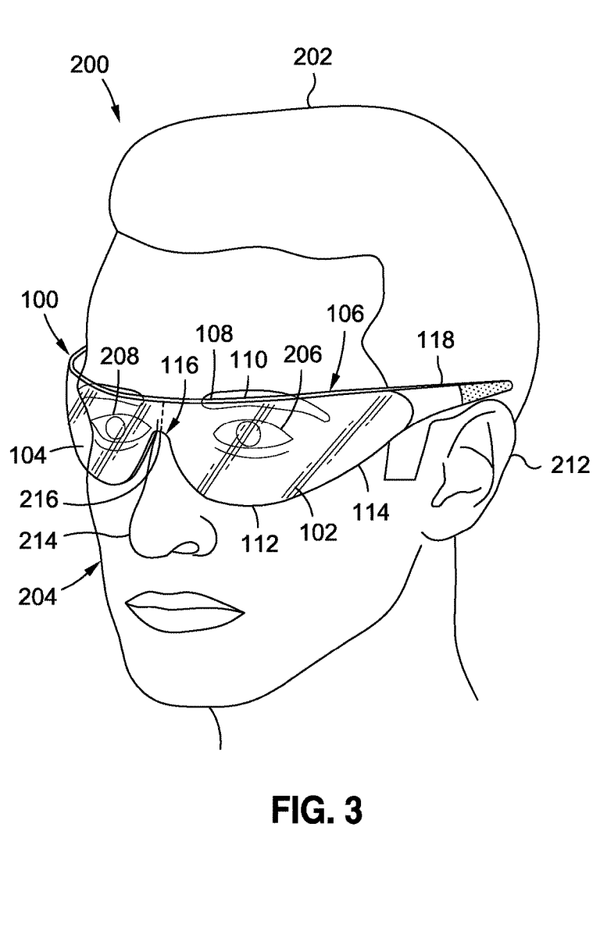
FIG. 3 is a perspective view of an example of the eye protection system of FIG. 2 worn on the head of a wearer.

FIG. 2 shows an example of an eye protection system 100 having a lens support 106 configured as a lens frame 108 for supporting or mounting the first lens 102 and the second lens 104. As shown in FIG. 3, the lens frame 108 may be a glasses frame configured to be worn on a head 202 of the wearer 200. The side-by-side arrangement of the first lens 102 and the second lens 104 may be complementary to a spacing between the first eye 206 (e.g., the left eye) and the second eye 208 (e.g., the right eye) of the wearer 200. The lens frame 108 and the first lens 102 and second lens 104 may be symmetrical about a vertical centerline (not shown) passing between the first lens 102 and the second lens 104. The lens frame 108 may have fixed or pivotable temple arms 118 extending rearwardly from a side of the respective first lens 102 and second lens 104. In addition, the lens frame 108 and/or the first lens 102 and the second lens 104 may includes a nose piece 116 configured to be supported on or over a bridge 216 of a nose 214 of the wearer 200. The rearwardly-extending temple arms 118 may be configured to engage the opposing ears 212 of the wearer 200 such as by extending over a top of the ears 212 and/or at least partially wrapping around the ears 212.

FIG. 4 is a top view of the eye protection system 100 of FIGS. 2-3 and illustrating laser beams 306 of laser light 304 directed at different angles toward the first eye 206 and the second eye 208 of a wearer 200. As described in greater detail below, the lens support 106 may be configured to support the first lens 102 and the second lens 104 on a wearer's head 202 in a manner allowing the first lens 102 and the second lens 104 to respectively filter light 300 oriented along a variety of different directions. In the example shown, the first lens 102 and the second lens 104 may collectively form a curved shape 110 or a wrap-around configuration shaped complementary to a curved contour of a human face 204. The first lens 102 and the second lens 104 may each have a main portion 112 located directly in front of the respective first eye 206 and second eye 208 when the lens frame 108 is worn by the wearer 200. In addition, the first lens 102 and the second lens 104 may each have an aft portion 114 extending aftwardly from the main portion 112 at least partially along a side of a wearer's head 202 when the lens frame 108 is worn by the wearer 200.

In this regard, the first lens 102 and the second lens 104 (FIG. 4) may each provide a lateral field of view of at least 90 degrees measured from a forwardly-directed line-of-sight 210 laterally centered between the first eye 206 and the second eye 208 (e.g., when viewed from a top-down direction) of a wearer's head 202 when the lens support 106 is worn by the wearer 200 (FIG. 4). In this manner, the first lens 102 and the second lens 104 may be configured to respectively protect the wearer's first eye 206 (FIG. 4) and second eye 208 from light 300 of the first wavelength(s) 308 and the second wavelength(s) 310 coming from a location generally forward of the wearer's face toward a location aft of the wearer's head 202 (FIG. 4). In addition, the first lens 102 and second lens 104 may be configured to respectively protect the first eye 206 and the second eye 208 from light 300 coming from a location laterally to the side of a forwardly-directed line-of-sight 210.

Referring still to FIG. 2-4, the first lens 102 and/or the second lens 104 may be removably mounted to the lens frame 108 (FIG. 2) such as to allow for substitution of lenses for filtering light 300 of a different wavelength relative to the wavelength filtered by the currently-installed lenses. For example, if it is determined that a specific wavelength or laser light 304 (FIG. 4) may be encountered by a pilot on a mission over a specific geographic region, a first lens 102 and a second lens 104 (FIG. 3) may be installed to filter wavelengths of laser light 304 predicted to be encountered by the pilot. In some examples of the eye protection system 100, the first lens 102 and/or the second lens 104 may be fixedly mounted or permanently mounted to the lens frame 108. In still further examples of the eye protection system 100, the first lens 102 and the second lens 104 (FIG. 4) may be formed as a single, monolithic sheet of material and which may be of constant thickness. The first lens 102 and the second lens 104 may be formed of glass, plastic, polycarbonate, high-index plastic, or other materials.

In an embodiment not shown, the lens frame 108 (FIG. 4) may be configured as a clip-on frame (not shown) configured to be clamped or mounted onto the frame of existing eyewear such as prescription eyewear and/or conventional sunglasses. Such a clip-on frame may be configured to be flipped or pivoted upwardly and downwardly. Although not shown, when the clip-on frame is pivoted upwardly, the first lens 102 and the second lens 104 (FIG. 4) may not filter light 300 (FIG. 4) directed toward the wearer's first eye 206 and second eye 208. When the clip-on frame is pivoted downwardly, the first lens 102 and the second lens 104 may filter light 300 of the respective first wavelength(s) 308 and the second wavelength(s) 310 in the manner described above.

As indicated above, the first lens 102 and the second lens 104 (FIG. 4) may be respectively configured to filter one or more first wavelengths 308 (FIG. 4) and one or more second wavelengths 310. In an embodiment, the first lens 102 and/or the second lens 104 may be configured to filter a single wavelength of light 300 (FIG. 4). For example, the first lens 102 may be configured to filter laser light 304 having a wavelength corresponding to the color green (e.g., a wavelength of approximately 633 nm from a helium-neon (HeNe) gas laser), and the second lens 104 may be configured to filter laser light 304 (FIG. 4) having a wavelength corresponding to the color red (e.g., wavelength of approximately 530 nm from an indium gallium phosphide (InGaP) laser diode). Table 1 below lists wavelength(s) of laser light 304 emitted by common laser devices, any one or more of which may be filtered by the first lens 102 and/or the second lens 104.

TABLE 1

| Laser type | Wavelength (nm) |
|---|---|
| Helium-Neon (gas) | 543.5, 594.1, 611.9, 632.8 |
| Argon (gas) | 488.0, 514.5 |
| Krypton (gas) | 647.1, 530.9 |
| Indium gallium phosphide | 635, 650, 670 |
| Gallium nitride | 400-480 |
| Indium gallium nitride | 510-530 |

In still further examples of the eye protection system 100 (e.g., FIG. 3), the first lens 102 and the second lens 104 may each be configured to filter multiple wavelengths of light 300 For example, the first lens 102 and the second lens 104 (FIG. 3) may each be configured to filter different wavelengths of laser light 304 simultaneously contained in a single laser beam 306 (FIG. 4). In another example, the first lens 102 and the second lens 104 may each be configured to simultaneously filter different wavelengths of laser light 304 emitted by different laser beams 306.

Preferably, the first lens 102 and the second lens 104 (e.g., FIG. 4) may be configured to respectively filter a first wavelength band 308 and a second wavelength band 310. In some examples, the first wavelength band 308 (FIG. 4) and the second wavelength band 310 may at least partially overlap such as in the visible spectrum. Having a region of overlap between the first wavelength band 308 and the second wavelength band 310 (FIG. 4) may avoid a spectral gap in the laser eye protection system 100 which may otherwise pose a risk for a situation or environment where neither eye is protected against laser light 304 (FIG. 4) resulting in the potential for vision impairment in both eyes (e.g., the left eye and the right eye).

Regarding embodiments wherein the first wavelength band 308 at least partially overlaps the second wavelength band 310, in one example, the first wavelength band 308 (FIG. 4) may include at least a portion of an ultraviolet spectrum (e.g., approximately 10-400 nm) and may extend from the ultraviolet spectrum into the visible spectrum (e.g., approximately 400-750 nm), and the second wavelength band 310 (FIG. 4) may include at least a portion of the near-infrared spectrum (e.g., approximately 750-2500 nm) and may extend from the near-infrared spectrum into the visible spectrum (approximately 400-750 nm). In another example, the first wavelength band 308 may extend from the ultraviolet spectrum to a wavelength in the range of approximately 550-600 nm into the visible spectrum, and the second wavelength band 310 may extend from the near-infrared spectrum to a wavelength in the range of approximately 550-600 nm. In a still further example, the first wavelength band 308 may extend from the ultraviolet spectrum to approximately 560 nm (e.g., ±20 nm), and the second wavelength band 310 may extend from approximately 560 nm to the near-infrared spectrum. In consideration of the relatively common laser light 304 (FIG. 4) colors of red and green, in any one of the examples disclosed herein, the first wavelength band 308 may include wavelengths in the range of approximately 620-750 nm (red), and the second wavelength band 310 may include wavelengths in the range of approximately 490-570 nm (green).

Figure 5:
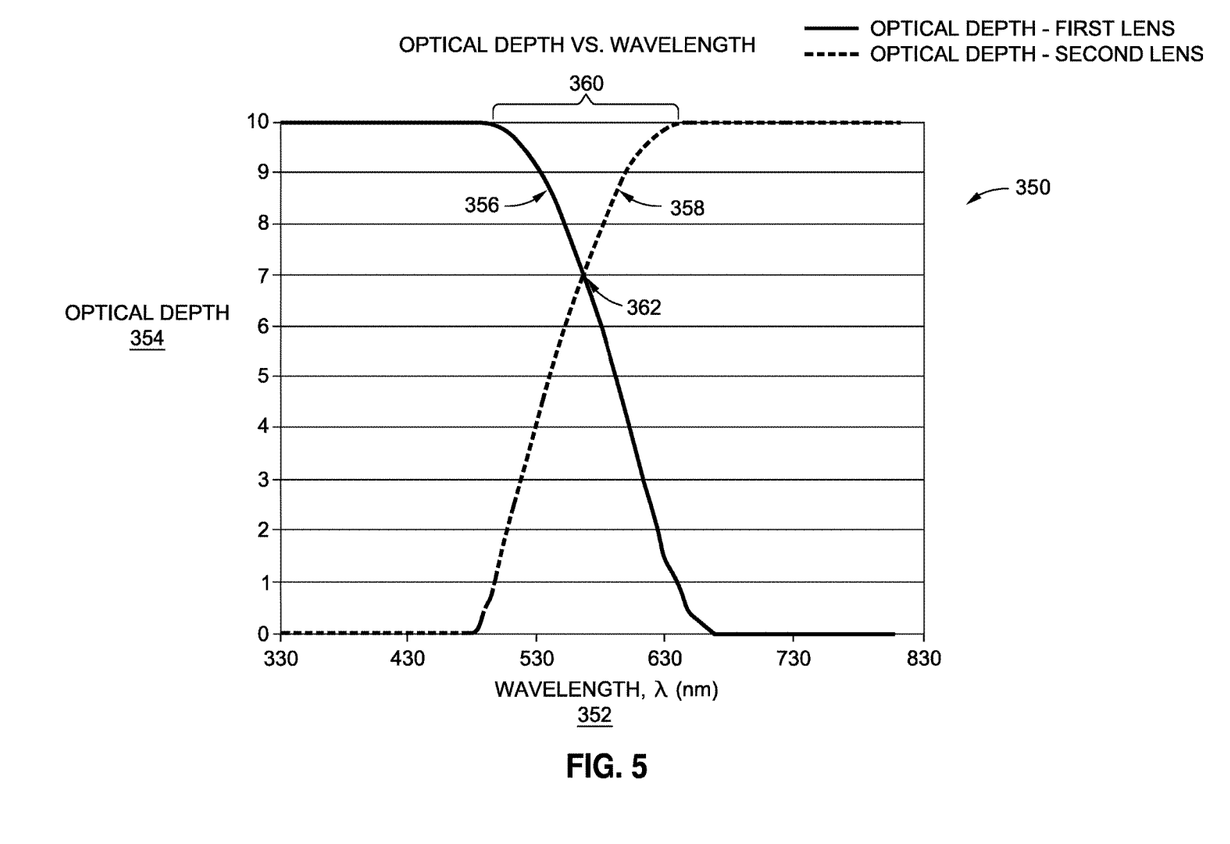
FIG. 5 is a graph plotting wavelength vs. optical depth for the first wavelength(s) and the second wavelength(s) respectively filtered by the first lens and the second lens.

FIG. 5 is a graph 350 plotting wavelength 352 vs. optical depth 354 for the first wavelength(s) 308 and the second wavelength(s) 310 respectively filtered by the first lens 102 and the second lens 104. Optical depth 354 of a lens may represent the opaqueness of the lens to radiation passing through the lens. In the present disclosure, the optical depth 354 of the first lens 102 or the second lens 104 (FIG. 4) may be described as the amount of radiation of a given wavelength respectively passing through the first lens 102 and the second lens 104. Optical depth 354 of a lens (e.g., of the first lens 102 or the second lens 104) may be defined as the natural logarithm of the ratio of incident light 300 to radiant power transmitted through the lens. In the present disclosure, in some examples, the first lens 102 (FIG. 4) and the second lens 104 may each have an optical depth 354 of at least 10 respectively in at least a portion of the first wavelength band 308 and in at least a portion of the second wavelength band 310. Such a relatively high optical depth 354 may be desirable for situations or environments where wavelength-agile lasers (e.g., dye lasers) may be encountered or where attacks by close-range lasers and/or by laser light 304 with strong wavelengths (e.g., high amplitude) are expected. In some examples, the first lens 102 and/or the second lens 104 may be configured as a multi-layer dielectric optical filter having one or more layers of material to tailor the reflectivity and/or transmissibility of the first lens 102 and/or the second lens 104 to achieve the desired optical depth 354 for one or more wavelengths.

FIG. 5 illustrates an example of the optical depth 354 of the first lens 102 and the second lens 104 with overlapping first wavelength band 308 and second wavelength band 310. As can be seen, the first lens 102 and the second lens 104 may respectively have a first lens decreasing optical depth 356 and a second lens decreasing optical depth 358 within an overlapping portion 360 of the first wavelength band 308 with the second wavelength band 310. For example, in the first lens decreasing optical depth 356, the first lens 102 may have an optical depth 354 that decreases or tapers from an optical depth 354 of at least 10 down to an optical depth 354 of 0 along the overlapping portion 360 of the first wavelength band 308 with the second wavelength band 310. Likewise, in the second lens decreasing optical depth 358, the second lens 104 may have an optical depth 354 that decreases or tapers from an optical depth 354 of at least 10 down to an optical depth 354 of 0 along the overlapping portion 360 of the first wavelength band 308 with the second wavelength band 310. In the example shown, the start of the decreasing optical depth 354 of the first lens 102 (e.g., from an optical depth 354 of at least 10) may be approximately (e.g., ±50 nm) the same wavelength as the wavelength where the decreasing optical depth 354 of the second lens 104 goes to 0, and/or vice versa.

In FIG. 5, the first lens 102 and the second lens 104 may have an optical depth 354 of at least 5 (e.g., approximately 7) at a crossover wavelength 362 (e.g., an intersection) of the first lens decreasing optical depth 356 with the second lens decreasing optical depth 358. In this regard, the first lens 102 and the second lens 104 may be configured such that the crossover wavelength 362 occurs where the laser light 304 approximately (e.g., ±50 nm) at such wavelength is predicted to be relatively weak or non-existent. For example, the crossover wavelength 362 may be in the range of approximately 550-600 nm which may correspond to the spectral gap occurring near approximately 560 nm, as indicated in Table 1 above. However, in situations or environments where attacks by strong or close-range lasers are expected at nearby wavelengths such as the 543.5 nm wavelength of a Helium-Neon laser beam, the first lens 102 may have an optical density of at least 10 from ultraviolet through 560 nm and the optical density may decrease at larger wavelengths (e.g., above 560 nm), and the second lens 104 may have an optical density of at least 10 from infrared through 560 nm and the optical density may decrease at smaller wavelengths (e.g., below 560 nm).

Figure 6:
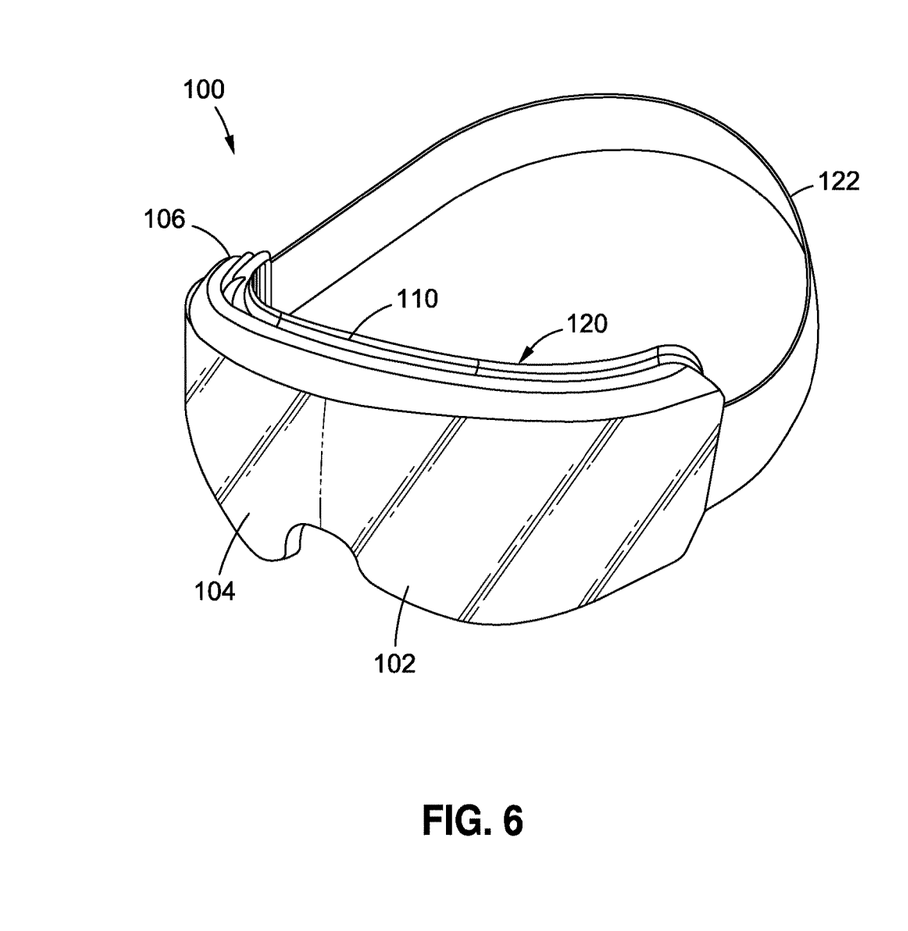
FIG. 6 is a perspective view of an example of an eye protection system wherein the lens support is configured as a goggles frame.

FIG. 6 shows an example of an eye protection system 100 wherein the lens support 106 is configured as a goggles frame 120 for mounting the first lens 102 and the second lens 104. The first lens 102 and the second lens 104 may be separate elements mounted to the goggles frame 120. Alternatively, the first lens 102 and the second lens 104 may be part of a single sheet of material mounted in the goggles frame 120. A strap 122 may be included for securing the goggles frame 120 to the head 202 of the wearer 200. The first and second lens 102, 104 may be configured in a wraparound style having a curved contour for providing a relatively wide field of vision for the wearer 200.

Figure 7:
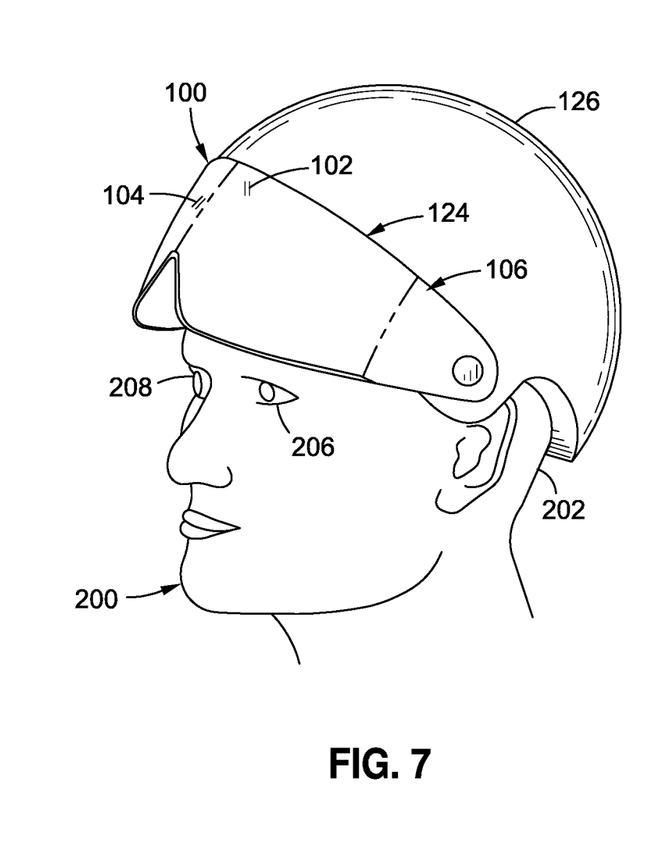
FIG. 7 is a perspective view of an example of an eye protection system wherein the first lens and the second lens are incorporated into a face shield mounted to a helmet and pivoted into an upward position.
Figure 8:
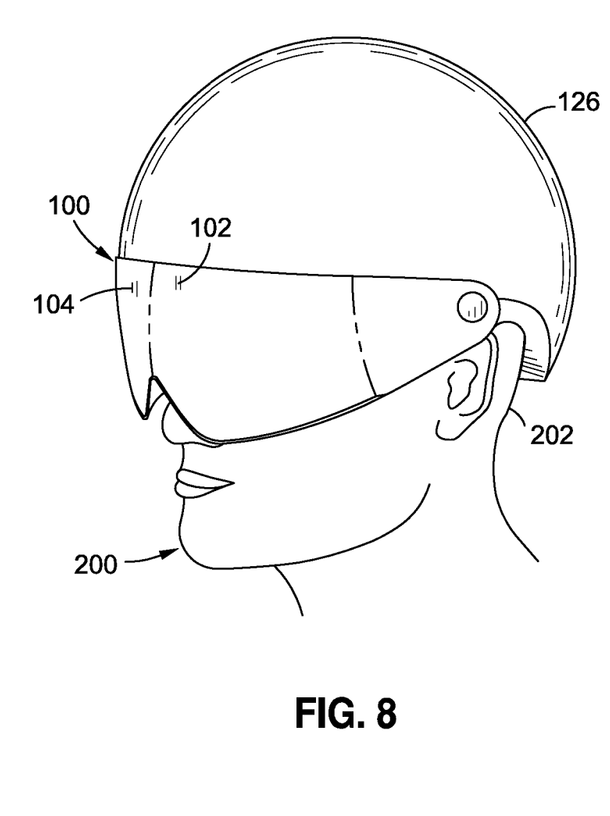
FIG. 8 is a perspective view of the eye protection system of FIG. 7 wherein the face shield is pivoted into a downward position covering the first eye and the second eye of the wearer.

FIG. 7 shows an example of an eye protection system 100 wherein the first lens 102 and the second lens 104 are incorporated into a face shield 124. In the example shown, the face shield 124 is mounted to a helmet 126 and is pivoted into an upward position such that the first eye 206 and the second eye 208 of the wearer 200 are unprotected from laser light 304 (e.g., FIG. 4). FIG. 8 shows the eye protection system 100 of FIG. 7 wherein the face shield 124 is pivoted into a downward position covering the first eye 206 and the second eye 208 of the wearer 200 for protection against light 300 of the first wavelength(s) 308 and second wavelength(s) 310, respectively. The face shield 124 may be configured to position the first lens 102 and the second lens 104 in side-by-side arrangement respectively in front of the first eye 206 and the second eye 208 of the wearer 200. In FIGS. 7-8, the pivotable nature of the face shield 124 may allow the wearer 200 to flip the face shield 124 up in zero-threat or low-threat environments, and upon approaching or encountering an environment or situation where there is a risk of a laser attack, the face shield 124 may be flipped down such the face shield 124 incorporating the first lens 102 and the second lens 104 may protect the wearer's eyes from light 300 in the respective first wavelength(s) 308 and second wavelength(s) 310. Although FIGS. 7-8 illustrate the face shield 124 mounted to a helmet 126, the face shield 124 may be pivotably or fixedly attached to a face shield frame (not shown) configured to be worn directly on the head 202 of the wearer 200.

In any of the examples disclosed herein, the first lens 102 and/or the second lens 104 may be provided with any one a variety of coatings or treatments applied to the front surface or back surface of the lenses 102, 104. For example, the first lens 102 and/or the second lens 104 may include one or more anti-reflective coatings to reduce glare, a scratch-resistant coating to prevent scratching of the lens surfaces, and/or an anti-fog coating to absorb moisture. Additionally or alternatively, a hydrophobic coating may be added to promote beading and runoff of water droplets on the lens surfaces, a tint may be provided to promote vision under certain lighting conditions such as fog or nighttime, and any one of a variety of other coatings or treatments may be applied to the first lens 102 and/or the second lens 104.

In any of the disclosed examples, the first lens 102 and the second lens 104 may each include a reflective optical coating or mirror coating 128 (e.g., FIG. 2) on an outer surface (e.g., opposite the inner surface facing the eyes) of the first lens 102 and the second lens 104. The mirror coating 128 (FIG. 2) may be formed on the outer surfaces of the first lens 102 and second lens 104 as a relatively thin metal layer of titanium, nickel, chromium, or other metals and/or alloys. Advantageously, the mirror coating 128 may cosmetically mask the color difference between the first lens 102 and the second lens 104 resulting from the different visible wavelength(s) respectively filtered by each lens 102, 104. In this regard, the mirror coating 128 may provide a common outward appearance (e.g., as observed by others) for the first lens 102 and second lens 104, and thereby conceal the difference in wavelength(s) 308, 310 respectively filtered by the lenses 102, 104. Only the wearer 200 (e.g., FIG. 2) would be able to determine that different regions of the visible spectrum are observed with each eye. Such a mirror coating 128 may make the eye protection system 100 more appealing to those who would benefit from wearing the system 100. In addition, the mirror coating 128 may reduce the intensity of ambient light 302 under certain conditions such as in bright sunlight.

Figure 9:
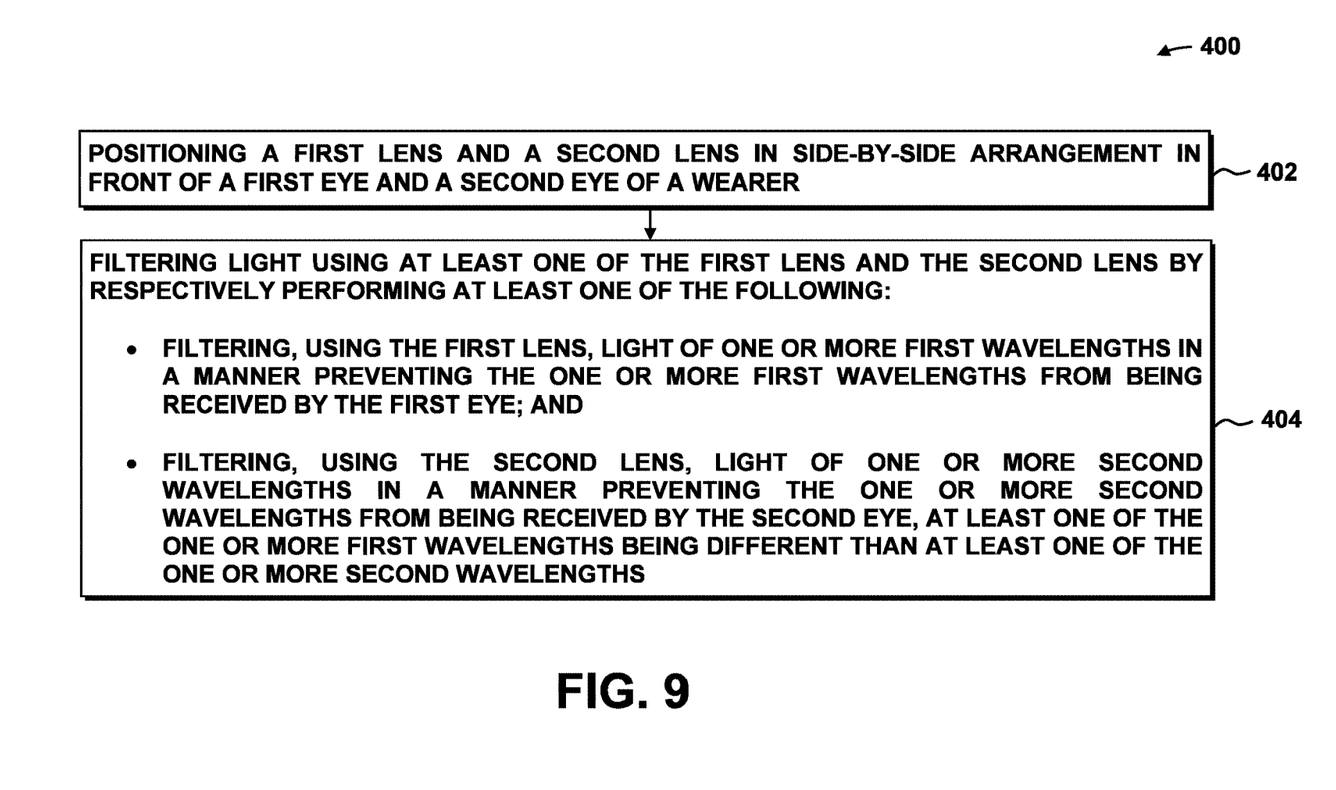
FIG. 9 is a flowchart having one or more steps that may be included in an eye protection method.

FIG. 9 is a flowchart having one or more steps that may be included in an eye protection method 400 for protecting a first eye 206 (e.g., a left eye) and a second eye 208 (a right eye) from laser light 304 (FIG. 4). Step 402 of the method 400 may include positioning the first lens 102 and the second lens 104 in side-by-side arrangement in front of the first eye 206 and the second eye 208 of a wearer 200 (FIG. 3). Step 404 of the method 400 may include filtering light 300 using the first lens 102 and/or the second lens 104 (FIG. 2) to respectively prevent light 300 of the first wavelength(s) 308 and/or second wavelength(s) 310 from being received by the respective first eye 206 and second eye 208 of the wearer 200.

For example, the method may include filtering light 300 of the on one or more first wavelengths 308 using the first lens 102 in a manner preventing the one or more first wavelengths 308 (FIG. 4) from being received by the first eye 206. In addition, the method may include filtering light 300 of one or more second wavelengths 310 (FIG. 4) using the second lens 104 in a manner preventing the one or more second wavelengths 310 from being received by the second eye 208 (FIG. 4). As indicated above, the one or more first wavelengths 308 may be different than at least one of the one or more second wavelengths 310. The first lens 102 and/or the second lens 104 (FIG. 4) may filter light 300 by absorbing light, reflecting light, or a combination of reflecting and absorbing light in the respective first wavelength(s) 308 and second wavelength(s) 310. The method may include passing light 300 through the first lens 102 (FIG. 4) and the second lens 104 in wavelengths respectively other than the first wavelengths 308 and the second wavelengths 310.

The method may additionally include using the first lens 102 and/or the second lens 104 to filter wavelengths of light 300 (FIG. 4) in the ultraviolet spectrum, the visible spectrum, and/or the infrared spectrum, as indicated above. The first lens 102 and/or the second lens 104 (FIG. 2) may filter light 300 by absorbing and/or reflecting light 300 in the respective first wavelength(s) 308 and second wavelength(s) 310 (FIG. 4). In some embodiments, the first lens 102 and/or the second lens 104 may comprise an absorptive filter to absorb light 300 in the respective first wavelength(s) 308 (FIG. 4) and secondly wavelength(s) while transmitting light 300 in other wavelengths. Alternatively or additionally, the first lens 102 and/or the second lens 104 (FIG. 2) may comprise an interference filter configured to cause overlap and interference of the peaks and troughs of the respective first wavelength(s) 308 and second wavelength(s) 310 to prevent transmission through the respective first lens 102 and second lens 104.

In some embodiments, the step of filtering the first wavelength 308 and second wavelength 310 using the respective first lens 102 and second lens 104 (FIG. 3) may include filtering a single wavelength of light, filtering different wavelengths of light simultaneously contained in a single laser beam 306 (FIG. 4), or filtering different wavelengths of light contained in different laser beams 306. However, in a preferred embodiment, the method may include using the first lens 102 and the second lens 104 to filter a respective first wavelength band 308 and a second wavelength band 310 (FIG. 5) which preferably at least partially overlap in the visible spectrum, as mentioned above. For example, the method may include using the first lens 102 (FIG. 4) to filter the first wavelength band 308 from the ultraviolet spectrum into the visible spectrum, and using the second lens 104 to filter the second wavelength band 310 from the near-infrared spectrum into the visible spectrum.

As indicated above, the first lens 102 and second lens 104 may be configured to filter the respective first wavelength band 308 and second wavelength band 310 with a specific optical depth 354. The first lens 102 and the second lens 104 may have a relatively high optical depth 354 (e.g., at least 10) respectively in at least a portion of the first wavelength band 308 and in at least a portion of the second wavelength band 310 (FIG. 5). The first lens 102 and the second lens 104 may respectfully have a first lens decreasing optical depth 356 (FIG. 5) and a second lens decreasing optical depth 358 within an overlapping portion 360 of the first wavelength band 308 with the second wavelength band 310, as shown in FIG. 5. The first lens 102 and the second lens 104 may be configured to filter the respective first wavelength band 308 and second wavelength band 310 with an optical depth 354 of at least 5 and a crossover wavelength 362 at the intersection of the first lens decreasing optical depth 356 with the second lens decreasing optical depth 358. As indicated above, in one example, the crossover wavelength 362 may be in the range approximate 550-600 nm.

As shown in FIGS. 2-4, the step 402 (FIG. 9) of the step of positioning the first lens 102 and the second lens 104 (FIG. 2) in front of the first eye 206 and the second eye 208 may include supporting the first lens 102 (FIG. 3) and the second lens 104 using a lens frame 108 (FIG. 4) which may be worn on the head 202 of the wearer 200. For example, the lens frame 108 may be a conventional glasses frame which one may simply put on when encountering a situation or environment wherein the threat of lasers is present. As shown in FIG. 6, the step 402 of positioning the first lens 102 and the second lens 104 in front of the first eye 206 and the second eye 208 may include supporting the first lens 102 and the second lens 104 in a goggles frame 120 (FIG. 5) which may be worn on the head 202 of a wearer 200. In a still further embodiment, as shown in FIG. 7-8, the step 402 of positioning the first lens 102 and the second lens 104 in front of the first eye 206 and second eye 208 may include supporting a face shield 124 on a wearer's head 202, wherein the face shield 124 incorporates the first lens 102 and the second lens 104. In one mode of operation, the face shield 124 may be pivotable to allow a wearer 200 to pivotably flip the face shield 124 up in environments that pose little or no threat of a laser attack, and flip the face shield 124 down when approaching or in an environment or situation where there is a risk of a laser light attack.

As mentioned above, the first lens 102 (FIG. 4) and the second lens 104 may be configured to jointly cover all anticipated wavelengths that may be encountered such as during a laser attack. Advantageously, each one of the first lens 102 and second lens 104 (FIG. 4) is relatively thin and therefore lightweight and inexpensive allowing the eye protection device to be comfortably worn for extended periods of time, and transmitting sufficient light 300 (FIG. 4) in unfiltered wavelengths to allow safe operation of a vehicle or the performance of other activities.

Additional modifications and improvements of the present disclosure may be apparent to those of ordinary skill in the art. Thus, the particular combination of parts described and illustrated herein is intended to represent only certain embodiments of the present disclosure and is not intended to serve as limitations of alternative embodiments or devices within the spirit and scope of the disclosure.

What is claimed is:

1. An eye protection system, comprising:
a first lens configured to filter light within a first wavelength band;
a second lens configured to filter light within a second wavelength band, at least a portion of the second wavelength band non-overlapping the first wavelength band;
a lens support configured to position the first lens and the second lens in laterally non-overlapping side-by-side arrangement respectively in front of a first eye and a second eye of a wearer in a manner preventing the first wavelength band from being received by the first eye and preventing the second wavelength band from being received by the second eye;

the first lens having a single first lens decreasing optical depth in which the optical depth decreases with increasing wavelength of the first wavelength band;

the second lens having a single second lens decreasing optical depth in which the optical depth decreases with decreasing wavelength of the second wavelength band; and the first lens decreasing optical depth at least partially overlapping the second lens decreasing optical depth within an overlapping portion of the first wavelength band with the second wavelength band.

2. The eye protection system of claim 1, wherein:
the first wavelength band and/or the second wavelength band is in at least one of an ultraviolet spectrum, a visible spectrum, and an infrared spectrum.

3. The eye protection system of 1, wherein at least one of the first wavelength band and the second wavelength band respectively comprises the following:
the first wavelength band includes at least a portion of an ultraviolet spectrum and extends from the ultraviolet spectrum into a visible spectrum; and
the second wavelength band includes at least a portion of a near-infrared spectrum and extends from the near-infrared spectrum into the visible spectrum.

4. The eye protection system of 1, wherein:
the first lens has an optical depth of at least 10 in at least a portion of the first wavelength band and/or the second lens has an optical depth of at least 10 in at least a portion of the second wavelength band.

5. The eye protection system of claim 1, wherein:
the first lens and the second lens have an optical depth of at least 5 at a crossover wavelength of the first lens decreasing optical depth with the second lens decreasing optical depth.

6. The eye protection system of claim 5, wherein:
the crossover wavelength is in a range of approximately 550-600 nm.

7. The eye protection system of claim 1, wherein:
the lens support is a lens frame configured to be worn on a head of the wearer.

8. The eye protection system of claim 1, wherein:
the first lens and the second lens collectively have a curved shape configured complementary to a curved contour of a human face.

9. The eye protection system of claim 1, wherein:
the first lens and the second lens each have a mirror coating on an outer surface of the first lens and the second lens.

10. An eye protection system, comprising:
a first lens configured to filter light in a first wavelength band at least partially overlapping a visible spectrum;
a second lens configured to filter light in a second wavelength band at least partially overlapping the visible spectrum, at least a portion of the first wavelength band non-overlapping the second wavelength band;
a lens support configured to position the first lens and the second lens in laterally non-overlapping side-by-side arrangement respectively in front of a first eye and a second eye of a wearer in a manner respectively preventing the first wavelength band from being received by the first eye and preventing the second wavelength band from being received by the second eye;

the first lens having a single first lens decreasing optical depth in which the optical depth decreases with increasing wavelength of the first wavelength band;

the second lens having a single second lens decreasing optical depth in which the optical depth decreases with decreasing wavelength of the second wavelength band; and the first lens decreasing optical depth at least partially overlapping the second lens decreasing optical depth within an overlapping portion of the first wavelength band with the second wavelength band.

11. The eye protection system of claim 10, wherein:
the lens support is a lens frame configured to be worn on a head of the wearer.

12. The eye protection system of claim 10, wherein:
the first lens and the second lens collectively have a curved shape configured complementary to a curved contour of a human face.

13. The eye protection system of claim 10, wherein:
the first lens and the second lens each have a mirror coating on an outer surface of the first lens and the second lens.

14. The eye protection system of claim 10, wherein:
the first lens has an optical depth of at least 10 in at least a portion of the first wavelength band and/or the second lens has an optical depth of at least 10 in at least a portion of the second wavelength band.

15. An eye protection method, comprising the following sequence of steps:
positioning a first lens and a second lens in laterally non-overlapping side-by-side arrangement respectively in front of a first eye and a second eye of a wearer;
filtering light using at least one of the first lens and the second lens by respectively performing at least one of the following:
filtering, using the first lens, light within a first wavelength band in a manner preventing the first wavelength band from being received by the first eye; and
filtering, using the second lens, light within a second wavelength band in a manner preventing the second wavelength band from being received by the second eye, at least a portion of the first wavelength band non-overlapping the second wavelength band;
the first lens having a single first lens decreasing optical depth in which the optical depth decreases with increasing wavelength of the first wavelength band;
the second lens having a single second lens decreasing optical depth in which the optical depth decreases with decreasing wavelength of the second wavelength band; and
the first lens decreasing optical depth at least partially overlapping the second lens decreasing optical depth within an overlapping portion of the first wavelength band with the second wavelength band.

16. The eye protection method of claim 15, wherein the step of filtering include:
filtering wavelengths in at least one of an ultraviolet spectrum, a visible spectrum, and an infrared spectrum.

17. The eye protection method of claim 15, wherein the steps of filtering the first wavelength band and the second wavelength band respectively include:
filtering the first wavelength band from an ultraviolet spectrum into a visible spectrum; and
filtering the second wavelength band from a near-infrared spectrum into the visible spectrum.

18. The eye protection method of claim 15, wherein:
the first lens has an optical depth of at least 10 in at least a portion of the first wavelength band and/or the second lens has an optical depth of at least 10 in at least a portion of the second wavelength band.

19. The eye protection method of claim 15, wherein at least one of the steps of filtering the first wavelength band and filtering the second wavelength band includes:
filtering different wavelengths of light simultaneously contained in a single laser beam;
filtering different wavelengths of light contained in different laser beams.

\* \* \* \* \*